US00PP10245P

United States Patent [19]

Enthoven

[11] Patent Number: Plant 10,245

[45] Date of Patent: Feb. 17, 1998

[54] GERANIUM PLANT NAMED 'MERIRICO'

[75] Inventor: Adrianus W. M. Enthoven, Wateringen, Netherlands

[73] Assignee: Enthoven Breeding B.V., Wateringen, Netherlands

[21] Appl. No.: 762,445

[22] Filed: Dec. 9, 1996

[51] Int. Cl.[6] ..... A01H 5/00

[52] U.S. Cl. ..... Plt./87.12

[58] Field of Search ..... Plt./87.12

*Primary Examiner*—James R. Feyrer
*Attorney, Agent, or Firm*—C. A. Whealy

[57] ABSTRACT

A new and distinct cultivar of Geranium plant named 'Meririco', characterized by its rounded, initially upright, then pendant growth habit; moderate growth rate and vigor; freely branching plant habit; fast rooting; medium green foliage color with distinct zonation pattern; numerous peduncles with seven to twelve flowers per umbel; semi-double red and dark pink flowers; and good weather and stress tolerance.

3 Drawing Sheets

The present invention relates to a new and distinct cultivar of Geranium plant, botanically known as *Pelargonium× peltatum*, and hereinafter referred to by the cultivar name Meririco.

The new cultivar is a product of a planned breeding program conducted by the inventor in Wateringen, The Netherlands. The objective of the breeding program was to develop new ivy geranium cultivars with double or semi-double flowers, fast rooting, tolerance to Botrytis, weather resistance, many peduncles with few flowers, compact and pendant growth habit, and interesting and unique flower colors.

The new cultivar originated from a cross made by the inventor of two unidentified propietary seedling selections. The cultivar Meririco was discovered and selected by the inventor as a flowering plant within the progeny of the stated cross in a controlled environment in Wateringen, The Netherlands, in June, 1994.

Plants of the male parent have single flowers whereas plants of the new cultivar have semi-double flowers. Plants of the new cultivar have a distinct zonation pattern on the foliage whereas plants of the female parent are devoid of a zonation pattern.

Asexual reproduction of the new cultivar by terminal cuttings taken at Wateringen, The Netherlands, has shown that the unique features of this new Geramium are stable and reproduced true to type in successive generations of asexual reproduction.

The following traits have been repeatedly observed and are determined to be the unique characteristics of 'Meririco'. These characteristics in combination distinguish 'Meririco' as a new and distinct cultivar:

1. Rounded; initially upright, then pendant growth habit.
2. Moderate growth rate and vigor.
3. Freely branching plant habit.
4. Fast rooting.
5. Medium green foliage color with distinct zonation pattern.
6. Numerous peduncles with seven to twelve flowers per umbel.
7. Semi-double red and dark pink flowers.
8. Good weather and stress tolerance.

The new Geranium can be compared to the nonpatented cultivar Tavira. Compared to plants of the cultivar Tavira, plants of the new Geranium are more compact, more vigorous, have a distinct zonation pattern on the foliage, and have more peduncles but fewer flowers per peduncle.

The accompanying colored photographs illustrate the overall appearance of the new cultivar, showing the colors as true as it is reasonably possible to obtain in colored reproductions of this type.

The first photograph comprises a top perspective view of a typical potted plant of 'Meririco'.

The second photograph comprises a top perspective view of a typical flower of 'Meririco'.

The third photograph comprises a top perspective view of typical leaves of 'Meririco'.

Foliage and flower colors in the photograph may appear different from the actual colors due to light reflectance.

The cultivar Meririco has not been observed under all possible environmental conditions. The phenotype may vary somewhat with variations in environment such as temperature and light intensity, without, however, any variance in genotype. The following observations, measurements and comparisons describe plants grown in Wateringen, The Netherlands, under commerical practice in a glass-covered greenhouse with day temperatures of 20C and night temperatures of 18C and light levels of 450 $Wm^2$.

In the following description, color references are made to The Royal Horticultural Society Colour Chart except where general terms of ordinary dictionary significance are used.

Classification:

*Botanical.*—*Pelargonium×peltatum* cv. 'Meririco'.

*Commercial.*—Ivy Geranium.

Parentage:

*Male parent.*—Unidentified proprietary seedling selection.

*Female parent.*—Unidentified proprietary seedling selection.

Propagation:

*Type cutting.*—Terminal cuttings.

*Time to initiate and develop roots.*—Summer: About 16 days at 20C. Winter: 16 to 20 days at 20C.

*Rooting habit.*—Vigorous, fast to root, freely branching.

Plant description:

*General appearance.*—Rounded; initially upright, then pendant growth habit. Appropriate for 10.5 to 12 cm containers. About 12 weeks are required to produce a finished plant from an unrooted cutting.

*Growth rate.*—Moderate.

*Vigor.*—Moderate.

*Plant height.*—About 25 cm.

*Branching habit.*—Very freely branching with about 8 lateral branches per plant. Pinching (removal of terminal apices) is usually not required.

*Internode length.*—About 4 cm.

*Foliage description.*—Arrangement: Opposite. Shape: Generally reniform with cordate to overlapping lobes at the base. Aspect: Slightly undulating. Size: Length: 3.5 to 4.5 cm. Width: 6 to 7.5 cm. Texture: Velvety, pubescent on abaxial surface. Margin: Lobed. Zonation: Distinct, 0.5 to 1 cm in width and 2 to 3 cm from margin. Color: Abaxial surface: 137A/137B. Adaxial surface: 137B/137C. Zonation, abaxial surface only: 147A. Venation pattern: Palmate. Petiole: Length: 4 to 5 cm. Diameter: 2 to 3 mm. Color: 143A/143B. Durability to rain, wind and stress conditions: Very good.

Flowering description:

*Flowering habit.*—Flowers arranged in umbels.

*Natural flowering season.*—Spring throughout summer.

*Flower longevity.*—Flowers last about 2.5 weeks on the plant. Flowers self-cleaning.

*Flowers borne.*—Flower buds develop in apical leaf axils. Umbels are displayed above the foliage.

*Umbels.*—Form: Rounded. Quantity of flowers per umbel: Usually 7 to 12. Diameter: 9 to 11 cm. Depth (height): 5 to 6 cm.

*Flowers.*—Form: Semi-double. Shape: Rounded. Diameter: About 5 cm. Depth (height): About 2.5 cm. Quantity of petals and petaloids per flower: About 11.

*Petals.*—Shape: Obovate with rounded apex. Arrangement: Rosette, overlapping. Aspect: Flat. Size: Length: 2.4 to 2.8 cm. Width: 1.5 to 1.7 cm. Texture: Satiny, smooth. Margin: Entire. Color: Opened flower, upper petals, adaxial surface: 43A/43B with medium purple stripes. Opened flower, upper petals, abaxial surface: 43C/43D. Opened flower, lower petals, adaxial surface: 52A. Opened flower, lower petals, abaxial surface: 52C.

*Petaloids.*—Shape: Irregular, generally obovate with rounded or slightly incised apex. Arrangement: Rosette, overlapping. Size: Length: 2 to 2.5 cm. Width: About 1.5 cm. Texture: Satiny, smooth. Margin: Entire. Color: 52A.

*Peduncle (umbel stem).*—Angle: Semi-erect. Size: Length: 12 to 15 cm. Diameter: About 3 mm. Texture: Pubescent. Color: Medium to light green.

*Pedicel (individual flower stem).*—Angle: Between 45° to 90° from vertical. Size: Length: 2.7 to 3 cm. Diameter: 2 to 3 mm. Texture: Pubescent. Color: Medium to light green.

*Flower bud.*—Shape: Narrowly elliptic. Size: Length: About 1.3 cm. Diameter: About 6 mm. Color: Medium to light green.

*Sepals.*—Shape: Narrowly lanceolate with acuminate apex. Arrangement: Rosette. Quantity: 5. Size: Length: About 1.5 cm. Width: 3 to 6 mm. Texture: Smooth. Margin: Entire. Color: Light green with red tones.

*Reproductive organs.*—Androecium: Stamen number: 3 to 5. Anther shape: Elongated oval. Anther size: About 3 mm. Pollen color: 179A. Gynoecium: Pistil number: 1. Pistil length: About 1 cm. Stigma shape: Decurrent. Stigma color: 61D. Style length: About 5 mm. Style color: Cream white to very light pink.

Disease resistance: No fungal, bacterial nor viral problems observed under commercial conditions.

Seed development: Seed production is very rarely observed.

It is claimed:

1. A new and distinct cultivar of Geranium plant named 'Meririco', as illustrated and described.

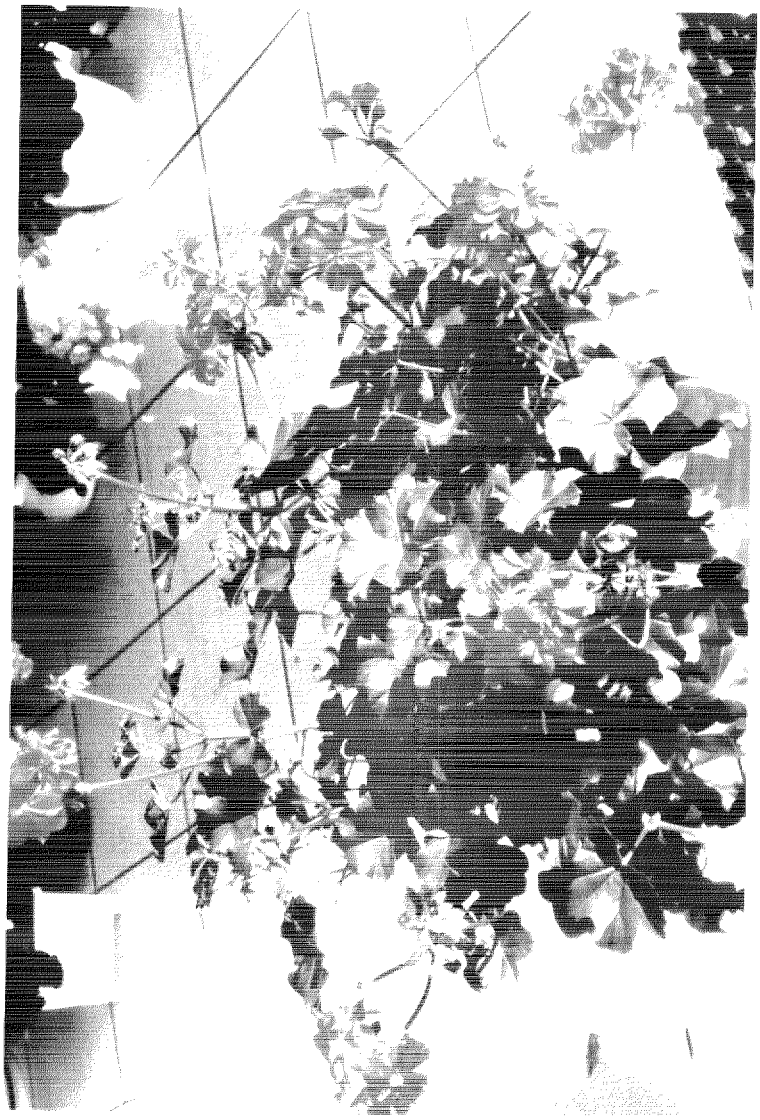

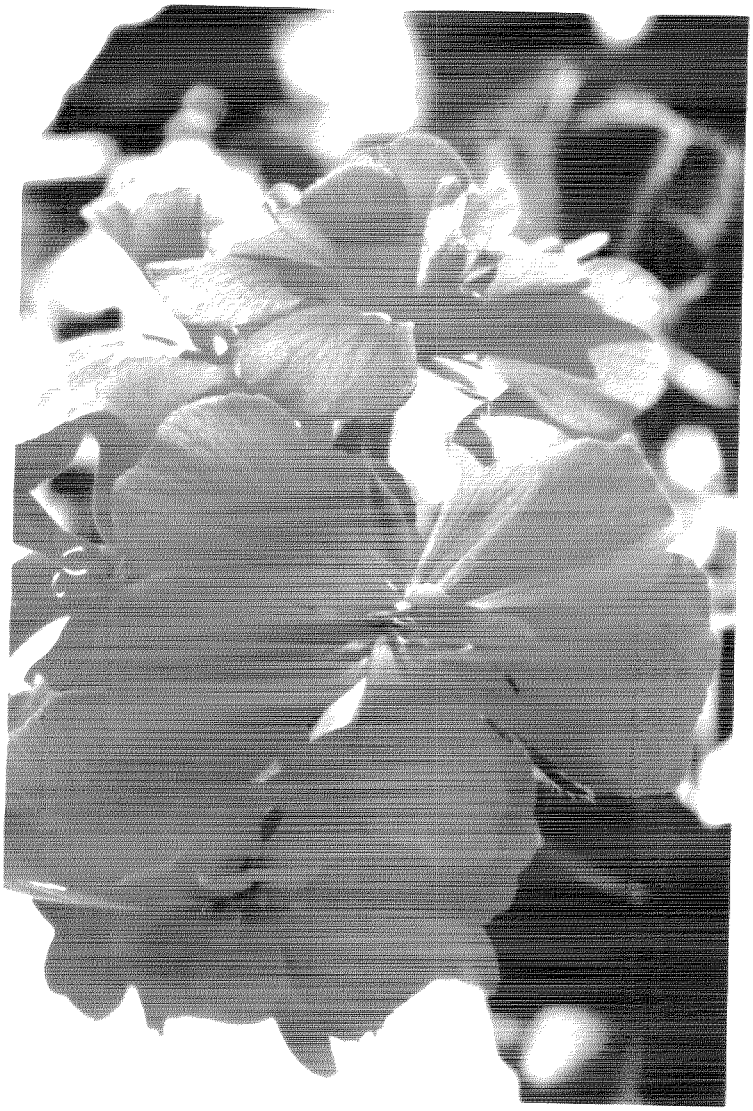

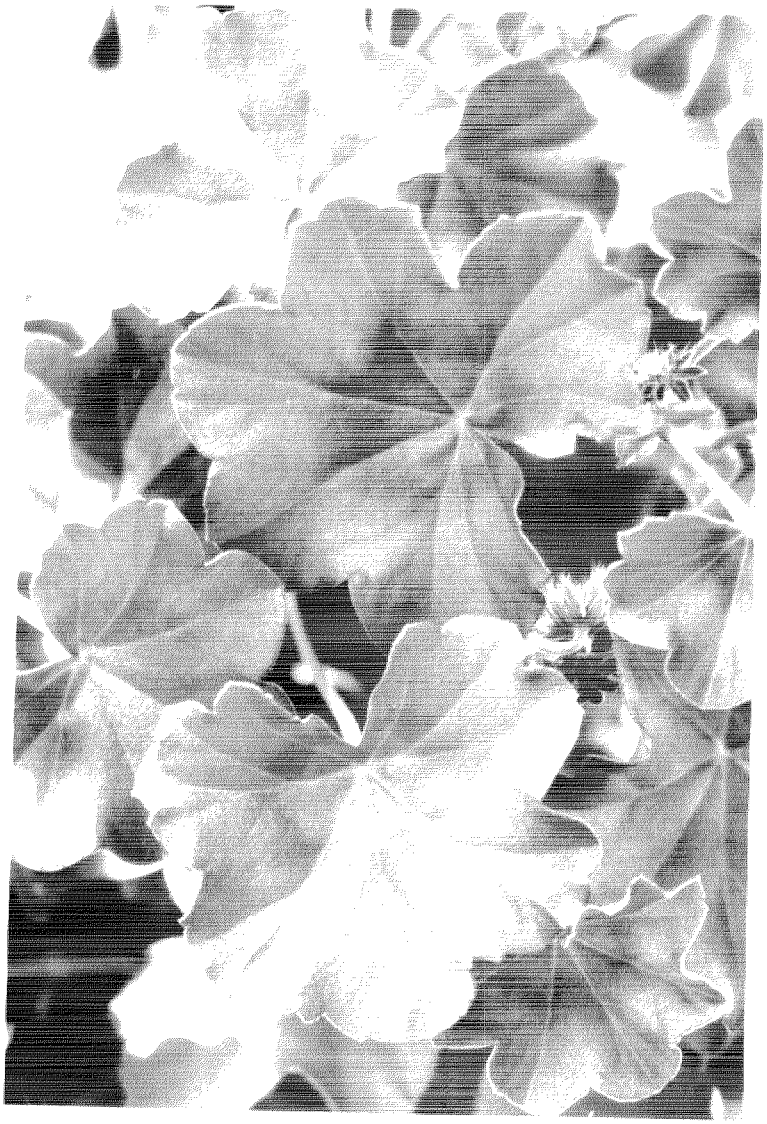

* * * * *